tion according to the present invention is excellent in feeling

United States Patent
Kashimoto

(10) Patent No.: US 6,524,597 B2
(45) Date of Patent: Feb. 25, 2003

(54) PRESSED POWDER COSMETIC COMPOSITION

(75) Inventor: Akio Kashimoto, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/745,544

(22) Filed: Dec. 26, 2000

(65) Prior Publication Data
US 2002/0012682 A1 Jan. 31, 2002

(30) Foreign Application Priority Data
Dec. 28, 1999 (JP) ............................. 11-374413

(51) Int. Cl.⁷ ..................... A61K 6/00; A61K 7/00; A61K 7/035
(52) U.S. Cl. ........................... 424/401; 424/69
(58) Field of Search ................... 424/401, 69

(56) References Cited
U.S. PATENT DOCUMENTS
3,632,744 A * 1/1972 Paulsen ................ 424/69
5,458,976 A * 10/1995 Horino ................. 428/405
5,578,311 A * 11/1996 Nagatani et al. .......... 424/401

FOREIGN PATENT DOCUMENTS
| JP | 56-108703 | 8/1981 |
| JP | 57-98205 | 6/1982 |
| JP | 58-203908 | 11/1983 |
| JP | 61-69711 | 4/1986 |
| JP | 1-96110 | 4/1989 |
| JP | 1-287010 | 11/1989 |
| JP | 05331019 A | * 12/1993 |

* cited by examiner

Primary Examiner—Thurman K. Page
Assistant Examiner—S. Howard
(74) Attorney, Agent, or Firm—Oblon, Spivak, McClelland, Maier & Neustadt, P.C.

(57) ABSTRACT

A pressed powder cosmetic composition comprising (A) a water-repellent and oil-repellent powder selected from the group consisting of a fluorine resin powder and a powder having a surface treated with a fluorine compound, (B) a film-forming polymer having a modulus of elasticity not greater than 200 kg/cm$^2$, and (C) an oil. The composition according to the present invention is excellent in feeling upon use and does not crack easily.

47 Claims, No Drawings

PRESSED POWDER COSMETIC COMPOSITION

BACKGROUND OF THE INVENTION

1. Field of the Invention

The present invention relates to a pressed powder cosmetic composition which has smooth and soft touch feeling, is excellent in feeling upon use and does not crack easily by an external force.

2. Description of the Related Art

A pressed powder cosmetic composition such as foundation, face powder or eye shadow is usually prepared by press molding, that is, solidification of a raw material composition, which has been filled in a container, by compression. Since a conventionally-employed pressed powder cosmetic composition contains an oil in a relatively small amount, a high molding pressure is required in order to overcome its weak powder-to-powder binding power. The press-molded product thus obtained is usually very hard and lacks soft touch feeling.

Lowering in the hardness of a pressed powder cosmetic composition, on the other hand, decreases its powder-to-powder binding power, which tends to cause cracking of the molded product of the composition by an external force.

A pressed powder cosmetic composition can also be prepared by the solvent method (Japanese Patent Application Laid-Open No. 108073/1981) wherein a mixed slurry, which has been obtained by mixing base materials including powder with a low-boiling-point organic solvent, is filled in a container, followed by removal of the solvent to solidify the slurry.

Although the solvent method is advantageous because it permits uniform filling of the mixture in a container, it is accompanied with the drawbacks that evaporation of a large amount of the solvent from the slurry during drying causes shrinkage or cracks, and the press-molded product in the container tends to be cracked by an external force or tends to develop caking.

SUMMARY OF THE INVENTION

An object of the present invention is therefore to provide a pressed powder cosmetic composition which has smooth and moisturized touch feeling, is excellent in feeling upon use, for example, easy release of powder, and does not crack easily.

The present inventors have found that a pressed powder cosmetic composition capable of attaining the above-described object is available by the use of a specific powder and a polymer having a specific modulus of elasticity in combination with an oil.

In the present invention, there is thus provided a pressed powder cosmetic composition, which comprises the following components (A), (B) and (C):

(A) a water-repellent and oil-repellent powder selected from the group consisting of fluorine resin powders and a powder having a surface treated with a fluorine compound, (B) a film-forming polymer having a modulus of elasticity not greater than 200 kg/cm$^2$, and (C) an oil.

The present invention makes it possible to provide a pressed powder cosmetic composition which has smooth and soft touch feeling, permits easy powder release therefrom and is therefore excellent in feeling upon use, is free from cracks and is not broken easily by an external force. The pressed powder cosmetic composition of the present invention is suited, for example, as makeup cosmetic compositions such as foundation, face powder, cheek rouge and eye shadow.

DETAILED DESCRIPTION OF THE PREFERRED EMBODIMENTS

The water-repellent and oil-repellent powder to be used as Component (A) in the present invention is selected from fluorine resin powders each originally having a water-repellent and oil-repellent surface and powders each having a surface treated with a fluorine compound. Examples of the powder to be treated with a fluorine compound include inorganic powders such as silicic acid, silicic anhydride, magnesium silicate, talc, sericite, mica, kaolin, red iron oxide, clay, bentonite, titanium-coated mica, bismuth oxychloride, zirconium oxide, magnesium oxide, zinc oxide, aluminum oxide, calcium sulfate, barium sulfate, magnesium sulfate, calcium carbonate, magnesium carbonate, iron oxide, ultramarine blue pigment, chromium oxide, chromium hydroxide, calamine, and carbon black, and complexes thereof; organic powders such as polyamide, polyester, polypropylene, polystyrene, polyurethane, vinyl resin, urea resin, phenol resin, silicon resin, acrylic resin, melamine resin, epoxy resin, polycarbonate resin, divinylbenzene styrene copolymer, silk powder, cellulose powder, metal salts of a long-chain alkyl phosphoric acid, and N-mono (long chain) alkylacyl basic amino acid and complexes thereof; and complex powder of the above-exemplified inorganic powder and organic powder.

As the fluorine compound for treating the surface of the above-exemplified powder, a polyfluoroalkylphosphoric acid (U.S. Pat. No. 3,632,744) represented by the following formula (a):

$$[C_xF_{2x+1}C_yH_{2y}O]_zPO(OH)_{3-z} \qquad (a)$$

wherein, x stands for 1 to 20, y stands for 1 to 5 and z stands for 1 or 2 can be mentioned as an example. Additional examples include fluoroalkyldi(oxyethyl)amine phosphate esters (Japanese Patent Application Laid-Open No. 250074/1987), fluoroalkyl-containing polymers (Japanese Patent Applications Laid-Open Nos. 167209/1980, 55481/1986, and 48803/1986), fluorine resins such as ethylene tetrafluoride (Japanese Patent Application Laid-Open No. 38707/1982), fluoroalcohols (Japanese Patent Applications Laid-Open No. 2251/1988 and 2252/1988), perfluoroepoxy compounds, sulfoamide type fluorophosphoric acid, perfluorosulfate salts, perfluorocarboxylate salts, perfluoroalkylsilanes (Japanese Patent Applications Laid-Open Nos. 318070/1989, 218603/1990, 160907/1989, 127477/1990, silane coupling agents such as "LP-1T, LP-4T and LP-8T", each trade name; product of Shin-Etsu Silicone Co., Ltd.), fluorine-containing halogenated hydrocarbons (flon) such as trichlorotrifluoroethane (Japanese Patent Application Laid-Open No. 318070/1989), fluoroalkyl-containing polyhydric alcohols, fluoroalkyl-containing polyoxyethylene compounds (Japanese Patent Applications Laid-Open Nos. 180810/1989 and 180811/1989), fluoroalkyl-containing sulfoamide carboxylic acids, and fluoroalkyl-containing acrylate ester copolymers (U.S. Pat. No. 3,632,744).

Out of these, perfluoroalkylphosphoric acids and salts thereof, polyfluoroalkylphosphoric acids, fluoroalkyldi(oxyethyl)amine phosphate esters, perfluorosulfate salts, perfluorocarboxylate salts and perfluoroalkylsilanes are particularly preferred.

There is no particular limitation imposed on the method of treating the surface of a powder. It may be carried out in a manner known per se in the art. Based on 100 parts of the powder, the fluorine compound is preferably added in an amount of 0.05 to 20 parts by weight, more preferably 2 to 10 parts by weight for the surface treatment.

The water-repellent and oil-repellent powder as described above is incorporated into the pressed powder cosmetic composition of the present invention together with other powder as needed. The water-repellent and oil-repellent powder is preferably used in an amount not less than 50 wt. % in the whole powder components from the viewpoint of feeling upon use. The total amount of the powder in the whole composition is preferably 55 to 99.9 wt. %, especially 65 to 99.9 wt. %, more especially 75 to 99.9 wt. %.

As the other powder, those mentioned above for the surface treatment with a fluorine compound can be used without the surface treatment.

The film-forming polymer to be used in the invention as Component (B) is preferred to have a modulus of elasticity not greater than 200 kg/cm$^2$, especially 1 to 200 kg/cm$^2$, more especially 1 to 100 kg/cm$^2$. When a polymer having a modulus of elasticity exceeding 200 kg/cm$^2$ is employed, the product available therefrom becomes poor in feeling upon use with deteriorated softness or smoothness.

In the present invention, the modulus of elasticity was measured in the following manner.

A sample film for measurement was prepared by weighing 10 g of a 10 wt. % solution or dispersion of a film-forming polymer on a TEFLON-made Petri dish of 5 cm in diameter, naturally drying it for 5 to 10 days to form a film (0.3 to 0.5 mm in thickness), and cutting the film into strips, each 15 mm long and 5 mm wide. After the sample was allowed to stand at 25° C. and relative humidity of 30% for at least 24 hours, it was fixed to a tensile test jig of a dynamic viscoelasticity measuring apparatus ("RHEOSPECTRA DVE-V4", product of UBM) and its modulus of elasticity was measured under the conditions of an oscillation frequency of 10 Hz and amplitude of 10 μm.

As the film-forming polymer having such a modulus of elasticity, that having a molecular weight of about 10,000 to 1,000,000 is preferred. Examples include polymers available by polymerization of at least one monomer having a polymerizable double bond, poly(N-acylalkyleneimine)-modified silicone (Japanese Patent Applications Nos. 112423/1993, 133352/1995 and 95705/1998), and vinyl-silicone block polymers (Japanese Patent Application Laid-Open No. 100307/1999). Examples of the monomer having a polymerizable double bond include hydrophilic monomers, for example, ethylenically unsaturated carboxylic acids such as acrylic acid, methacrylic acid, maleic acid and fumaric acid, unsaturated carboxylate esters such as hydroxyethyl (meth)acrylate and polyethylene glycol mono (meth)acrylate, unsaturated carboxylic amides such as (meth)acrylamide and N-diacetone acrylamide, and amino-containing unsaturated carboxylate esters such as aminoethyl (meth)acrylate, N,N-dimethylaminoethyl (meth) acrylate, N,N-diethylaminoethyl (meth)acrylate and N,N,N-trimethylaminoethyl (meth)acrylate and salts thereof; and hydrophobic monomers, for example, aromatic vinyl compounds such as styrene, α-methylstyrene, chlorostyrene and alkylstyrenes; acrylate esters and methacrylate esters such as methyl (meth)acrylate, ethyl (meth)acrylate, propyl (meth) acrylate, butyl (meth)acrylate, 2-ethylhexyl (meth)acrylate, t-butyl (meth)acrylate, 2-ethylhexyl (meth)acrylate, t-butyl (meth)acrylate and cyclohexyl (meth)acrylate; vinyl cyanide compounds such as acrylonitrile and methacrylonitrile, vinyl esters such as vinyl acetate, vinyl halides such as vinyl chloride and vinylidene chloride, fluorine monomers such as trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate, and silicone macromonomers as represented by any one of the following formulas (1) to (5):

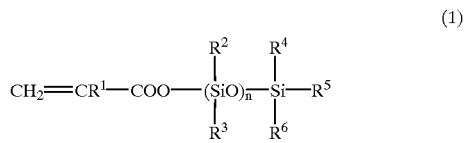

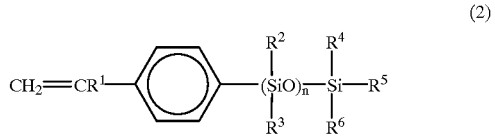

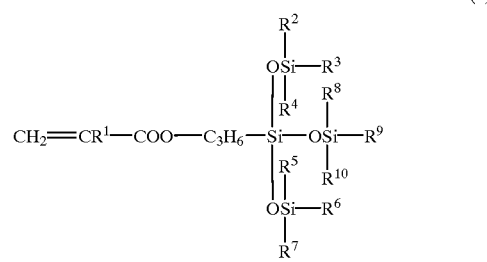

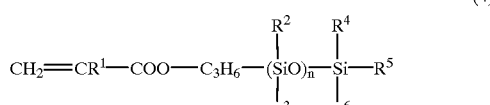

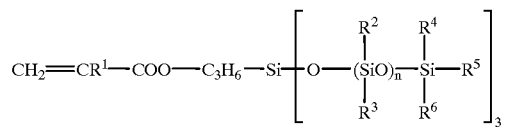

wherein, $R^1$ represents a hydrogen atom or a methyl group, $R^2$ to $R^{10}$ each independently represents a $C_{1-6}$ alkyl group, $C_{1-6}$ alkoxy group or phenyl group and n stands for 1 to 500.

As the poly(N-acylalkyleneimine)-modified silicone, preferred are those each having a poly(N-acylalkyleneimine) segment made of recurring units each represented by the following formula (6):

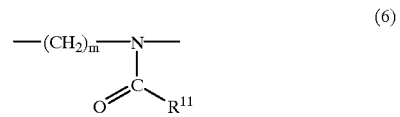

wherein, $R^{11}$ represents a hydrogen atom or a $C_{1-22}$ alkyl, cycloalkyl, aralkyl or aryl group and m stands for 2 or 3, and an organopolysiloxane segment. Said poly(N-acylalkyleneimine) segment is produced by ring-opening polymerization of 2-oxazoline monomers or 2-oxazine monomers. Said poly(N-acylalkyleneimine) segment is bonded to the organopolysiloxane segment at the end thereof or as the side chain thereof through a hetero-atom-containing alkylene group. It contains the poly(N-acylalkyleneimine) segment and the organopolysiloxane segment at a weight ratio ranging from 1:50 to 20:1; and having a molecular weight of 10,000 to 500,000, particularly 50,000 to 300,000.

As the vinyl-silicone block polymer, that having, as structural units, a silicone polymer unit represented by the following formula (7):

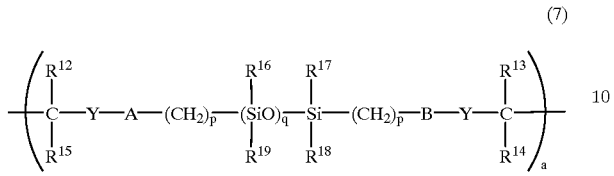

(7)

wherein $R^{12}$, $R^{13}$, $R^{14}$ and $R^{15}$ are the same or different and each independently represents a hydrogen atom, a $C_{1-6}$ alkyl group or a nitrile group, $R^{16}$, $R^{17}$, $R^{18}$ and $R^{19}$ are the same or different and each independently represents a hydrogen atom or an alkyl or aryl group which may be substituted with a halogen atom, Y represents a linear or branched, saturated or unsaturated $C_{1-10}$ hydrocarbon group which may be substituted by a halogen atom, A represents a —CONH— or —COO— group, B represents an —NHCO— or —OCO— group with the proviso that when A represents a —CONH— group, B represents a —NHCO— group, while when A represents a —COO— group, B represents an —OCO— group, q stands for 0 to 200, p stands for 0 to 6 and a stands for 2 to 300, and a vinyl monomer unit free of a fluorine atom; the total number of the silicone monomers constituting the silicone polymer unit of the formula (7) being 5 to $10^6$, the total number of the vinyl monomers being 10 to $10^6$, the sum of the total numbers of the silicone monomers and the vinyl monomers being $10^2$ to $10^6$, and a ratio of the total number of the silicone monomers to the total number of the vinyl monomers falling within a range of from 1:99 to 99:1 can be given as one example.

As Component (B), the film-forming polymer is preferably used in an amount of 0.1 to 15 wt. %, especially 0.5 to 10 wt. %, more especially 1 to 8 wt. % based on the whole composition.

As the oil of Component (C), oils including a fluorine oil are preferred. Examples of the fluorine oil include perfluoropolyether, perfluorodecalin, perfluorooctane and fluorine-modified silicone oils as described in Japanese Patent Application Laid-Open No. 180828/1999. As the perfluoropolyether, commercially available products such as FOMBLIN (trade name; product of Ausimont) and DEMNUM (trade name; product of Daikin Industries, Ltd.) can be mentioned by way of example. The oil (C) is preferred to contain the fluorine oil in an amount of at least 50 wt. % in order to attain good feeling upon use. Other oil components are those having no fluorine atoms. The oil (C) is preferably incorporated in an amount of 0.1 to 30 wt. %, especially 0.5 to 25 wt. %, more especially 0.5 to 20 wt. % based on the whole composition.

Examples of the above-mentioned oil components other than the fluorine oils include solid or semisolid oils such as vaseline, lanolin, ceresin, microcrystalline wax, carnauba wax, candelilla wax, higher fatty acids and higher alcohols; and liquid oils such as squalane, liquid paraffin, ester oils, diglyceride, triglyceride and silicon oils.

The pressed powder cosmetic composition according to the present invention preferably has a hardness, as measured by ASKER rubber hardness tester, C1L model, of 75 or less, especially 10 to 75; a porosity of 0.35 to 0.5, especially 0.37 to 0.5; and an impact resistance of 5 or greater, especially 7 or greater, because the composition having such properties is excellent in feeling upon use and crack resistance. The pressed powder cosmetic composition in the form of a foundation preferably has a hardness of 10 to 70, especially 10 to 67, while that in the form of an eye shadow preferably has a hardness of 30 to 75, especially 50 to 75.

The hardness is determined by directly measuring the hardness of the press molded product by ASKER rubber hardness tester (durometer), C1L Model (product of Kobunshi Keiki Co., Ltd.). In Preparation Examples which will be described later, the measurement was conducted by using a sample which had been filled in an aluminum pan of 54 mm in diameter and 4 mm in depth, press molded and then dried. The porosity was determined from the weight and volume of the molded product and true specific gravity of a powder bulk, based on the following equation:

$$\text{Porosity} = 1 - \frac{\text{Weight of molded product}}{\text{True specific gravity of powder bulk}} \times \frac{1}{\text{Volume of molded product}}$$

In the above equation, the term "molded product" means a cosmetic composition after molding and drying, while the term "powder bulk" means a dried powder mixture which has not been molded and its true specific gravity is measured using "AccuPyc, Model 1330", trade name; product of SHIMADZU Corporation).

The impact resistance was evaluated by the dropping frequency at which abnormalities such as cracks occurred when the above-described molded product was dropped in repetition from the height of 50 cm onto a plywood board of 25 mm thick.

To the pressed powder cosmetic composition of the present invention, it is possible to add, in addition to the above-described components, a surfactant, antiseptic, antioxidant, colorant, thickener, pH regulator, perfume, ultraviolet absorber, humectant, blood flow promoter, coolant, antiperspirant, bactericide, and/or skin activator as needed within an extent not impairing the advantages of the present invention.

The pressed powder cosmetic composition of the present invention can be prepared, for example, by mixing, the powder, oil, film-forming polymer having a modulus of elasticity not greater than 200 kg/cm$^2$ and volatile solvent and then evaporating the volatile solvent to solidify the mixture.

Examples of the volatile solvent include water, low-boiling-point alcohols such as ethanol and isopropyl alcohol, hexane, isoparaffin, acetone, ethyl acetate and volatile silicone oil. Out of them, water and an aqueous alcohol solution are preferred.

Upon mixing, it is preferred to add the powder in an amount of 40 to 94.9 wt. %, especially 50 to 94.9 wt. %, the film-forming polymer in an amount of 0.1 to 14 wt. %, especially 0.5 to 10 wt. % and the volatile solvent in an amount of 5 to 40 wt. %. When the volatile solvent is added in an amount of 5 to 40 wt. %, the mixture thus obtained is in the form of a slightly wet powder. Amounts of the volatile solvent exceeding 40 wt. % are not preferred, because the mixture thus obtained becomes slurry as described in Japanese Patent Application Laid-Open No. 108703/1981, and during drying, shrinkage of the solid content occurs as a large amount of the solvent evaporates from the slurry, which causes a reduction in the porosity and makes the pressed product so hard as even to cause problems such as small cracks.

The pressed powder cosmetic composition is available by filling the mixture of the powder, oil, film-forming polymer and volatile solvent in a container and molding under pressure and then evaporating the solvent under proper conditions (temperature, pressure, time). The conditions of compression molding and solvent evaporation can be determined as needed depending on the kind, size or shape of a target pressed powder cosmetic product.

EXAMPLES

Preparation Example 1

In a reaction vessel, charged were 150 parts by weight of water, 3 parts by weight of sodium lauryl sulfate and 0.5 part by weight of potassium persulfate. Nitrogen gas was allowed to flow in the container to remove a dissolved oxygen. 17 parts by weight of styrene, 33 parts by weight of 2-ethylhexyl acrylate and 2.0 parts by weight of n-dodecylmercaptane were charged in a dropping funnel. The reaction vessel was heated to 70° C. while the mixture therein was stirred. The above-described monomer mixture was then added dropwise from the dropping funnel to the vessel over 3 hours. After completion of the dropwise addition, maturation was conducted over 3 hours. From the reaction mixture, a small amount of an agglomerate was removed, whereby an alkyl acrylate copolymer emulsion having a solid content of 45 wt. % was obtained. The emulsion was then diluted with water into a 12 wt. % emulsion.

Preparation Example 2

In a reaction vessel, were charged 5 parts by weight of methacrylic acid, 22 parts by weight of methyl methacrylate, 33 parts by weight of n-butyl acrylate, 40 parts by weight of a macroazo polymerization initiator ("VPS-0501", trade name; product of Wako Pure Chemicals, average molecular weight: 30000 to 40000) having a polydimethylsiloxane structure, and 200 parts by weight of methyl ethyl ketone. Under stirring at room temperature, nitrogen gas was allowed to flow through the vessel for about 1 hour to remove the dissolved oxygen. Under stirring, the reaction vessel was heated to 80° C. and polymerization was conducted for 6 hours, followed by maturation at 85° C. for 2 hours, whereby a transparent viscous solution was obtained. The resulting solution was diluted with 100 parts by weight of methyl ethyl ketone, neutralized with 5 parts by weight of 1N-NaOH and then added with 600 parts by weight of deionized water. From the resulting solution, methyl ethyl ketone was distilled off under reduced pressure. The residue was diluted with deionized water, whereby an emulsion having a solid content of 12 wt. % was obtained.

Example 1

A pressed powder foundation having the composition as described in Table 1 was prepared and its softness, smoothness and powder releasability were evaluated based on the below-described standards. Namely, after the powder components were mixed in a Henschel mixer, an oil (perfluoropolyether and/or dimethylpolysiloxane) and then a film-forming polymer were added successively and they were mixed. The resulting mixture was filled in a pan, followed by press molding and drying, whereby a pressed powder foundation was obtained.

With regards to impact resistance, evaluation was conducted in the following manner. A pressed powder foundation was prepared by filling the mixture in a aluminum pan of 54 mm in diameter and 4 mm in depth, press molding it at a pressure of 10 kg/cm$^2$ and dried at 50° C. for 3 hours under normal pressure. The impact resistance of the product thus obtained was evaluated by the dropping frequency at which abnormalities such as cracks occurred when it was repeatedly dropped from the height of 50 cm onto a plywood board of 25 mm thick. The results are collectively shown in Table 1. The invention products have been found to have a soft touch feeling, be excellent in smoothness and feeling upon use such as powder releasability and have good impact resistance, compared with the comparative products.

(Standards for Evaluation)
A: excellent
B: good
C: slightly poor
D: poor

TABLE 1

| Component (wt. %) | Invention product | | | | | Comparative Product | | | |
| --- | --- | --- | --- | --- | --- | --- | --- | --- | --- |
| | 1 | 2 | 3 | 4 | 5 | 1 | 2 | 3 | 4 |
| Fluorine-treated mica (average particle size: 15 μm)*[1] | 25.0 | 25.0 | 25.0 | 12.5 | 20.0 | 15.0 | | 25.0 | 40.0 |
| Fluorine-treated talc (average particle size: 10 μm)*[1] | 17.0 | 17.0 | 17.0 | 17.0 | 17.0 | 17.0 | | 17.0 | 27.0 |
| Silicone-treated mica (average particle size of 15 μm)*[1] | | | | 12.5 | | | 42.0 | | |
| Fluorine-treated spherical silicone resin (average particle size of 12 μm)*[1] | 10.0 | 10.0 | | 10.0 | 10.0 | 10.0 | 10.0 | 10.0 | 10.0 |
| Fluorine-treated spherical silicone resin (average particle size of 4.5 μm)*[1] | | | 5.0 | | | 5.0 | 5.0 | | |
| Fluorine-treated titanium oxide*[1] | 5.0 | 5.0 | 5.0 | 5.0 | 5.0 | 5.0 | 5.0 | 5.0 | 5.0 |
| Fluorine-treated coloring pigment*[1] | 3.0 | 3.0 | 3.0 | 3.0 | 3.0 | 3.0 | 3.0 | 3.0 | 3.0 |
| Dimethylpolysiloxane*[2] | | | | 5.0 | | | 10.0 | | |
| Perfluoropolyether*[3] | 15.0 | 15.0 | 15.0 | 10.0 | 15.0 | 15.0 | | 15.0 | 15.0 |
| A 12 wt. % aqueous dispersion of poly(N-acylalkyleneimine)-modified silicone*[4] (modulus of elasticity: 5.3 kg/cm$^2$) | 25.0 | 25.0 | | 25.0 | | | 25.0 | | |

TABLE 1-continued

|  | Invention product | | | | | Comparative Product | | | |
|---|---|---|---|---|---|---|---|---|---|
| Component (wt. %) | 1 | 2 | 3 | 4 | 5 | 1 | 2 | 3 | 4 |
| A 12 wt. % water-dispersed emulsion of the alkyl acrylate copolymer of Preparation Example 1 (modulus of elasticity: 50 kg/cm$^2$) | | 30.0 | | | | | | | |
| A 12 wt. % water-dispersed emulsion of the alkyl acrylate copolymer of Preparation Example 2 (modulus of elasticity: 5.9 kg/cm$^2$) | | | | 30.0 | | | | | |
| A 12 wt. % water-dispersed emulsion of an alkyl acrylate copolymer*$^5$ (modulus of elasticity: 255 kg/cm$^2$) | | | | | | 30.0 | | | |
| Purified water | | | | | | | | 25.0 | |
| Press molding pressure (kg/cm$^2$) | 5.0 | 10.0 | 15.0 | 10.0 | 10.0 | 10.0 | 10.0 | 10.0 | 900.0 |
| Hardness | 51.0 | 61.0 | 65.0 | 67.0 | 59.0 | 78.0 | 69.0 | 20.0 | 80.0 |
| Porosity | 0.46 | 0.38 | 0.37 | 0.36 | 0.38 | 0.34 | 0.34 | 0.54 | 0.30 |
| Softness | A | B | B | B | B | D | D | D | D |
| Smoothness | A | A | B | B | B | D | C | C | C |
| Powder releasability | A | A | B | B | B | D | C | B | B |

*$^1$Treated with a perfluoroalkylphosphate ester diethanolamine salt ("AG530", trade name; product of Asahi Glass Co., Ltd.)
*$^2$"KF96A" (6 mPa · s), trade name; product of Shin-Etsu Chemical Co., Ltd.)
*$^3$Perfluoropolymethyl isopropyl ether ("FOMBLIN HC/K", trade name; product of Ausimont)
*$^4$A 12 wt. % aqueous dispersion obtained by dissolving the compound as described in Synthesis Example 7 of Japanese Patent Application Laid-Open No. 95705/1998 in ethanol, followed by replacement of a solvent.
*$^5$A 12 wt. % emulsion obtained by diluting "YODOSOL GH-800" (trade name; product of Kanebo NSC, Ltd.) with water.

Example 2

In a similar manner to Example 1 by using a 12 wt. % aqueous dispersion of a poly(N-acylalkyleneimine)-modified silicone, an eye shadow having the composition as shown in Table 2 was prepared. Evaluation results are shown in Table 2. The invention product has been found to have eminent impact resistance and have good feeling upon use, compared with the comparative product.

TABLE 2

| | Invention Product 6 | Comparative Product 5 |
|---|---|---|
| Fluorine-treated mica (average particle size of 15 μm)*$^1$ | 15.0 | 15.0 |
| Fluorine-treated talc (average particle size of 6 μm)*$^1$ | 15.91 | 15.91 |
| Fluorine-treated nylon powder (average particle size of 5 μm) | 5.0 | 5.0 |
| Zinc stearate | 5.0 | 5.0 |
| Paraben | 0.1 | 0.1 |
| Red color NO. 202 | 0.01 | 0.01 |
| Yellow color No. 401 | 0.2 | 0.2 |
| Blue color No. 404 | 0.4 | 0.4 |
| Black iron oxide | 0.03 | 0.03 |
| Titanium oxide | 0.05 | 0.05 |
| Fluorine-treated mica titanium*$^1$ | 40.0 | 40.0 |
| Beeswax | 2.0 | 2.0 |
| Squalane | 3.0 | 3.0 |
| 2-Ethylhexyl palmitate | 3.0 | 3.0 |
| Perfluoropolyether*$^2$ | 2.0 | 2.0 |
| A 12 wt. % aqueous dispersion of poly(N-acylalkyleneimine)-modified silicone | 8.3 | — |
| Purified water | — | 8.3 |
| Press molding pressure (kg/cm$^2$) | 400 | 400 |
| Hardness | 72 | 71 |
| Porosity | 0.37 | 0.35 |
| Impact resistance | 14 | 4 |

*$^1$Treated with a perfluoroalkylphosphoric acid [(C$_8$F$_{17}$CH$_2$CH$_2$O)$_2$P(O))OH]
*$^2$A perfluoroalkylpolymethyl isopropyl ether ("FOMBLIN HC/K", trade name; product of Ausimont)

What is claimed is:

1. A pressed powder cosmetic composition, comprising:
    (A) a powder selected from the group consisting of a fluorine resin powder and a powder having a surface treated with a fluorine compound,
    (B) a film-forming polymer having a modulus of elasticity not greater than 200 kg/cm$^2$, and
    (C) a fluorine oil.

2. The pressed powder cosmetic composition according to claim 1, wherein the pressed powder composition has a hardness of at most 75 as measured by ASKER rubber hardness tester C1L Model, a porosity of 0.35 to 0.5 and an impact resistance of at least 5 in terms of dropping frequency at which abnormalities occur when a press molded product is dropped in repetition from the height of 50 cm onto a plywood board of 25 mm thick.

3. The pressed powder cosmetic composition according to claim 1, wherein component (A) is at least one powder selected from the group consisting of inorganic powder and organic powder.

4. The pressed powder cosmetic composition according to claim 1, wherein component (A) is at least one inorganic powder selected from the group consisting of silicic acid, silicic anhydride, magnesium silicate, talc, sericite, mica, kaolin, red iron oxide, clay, bentonite, titanium-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine blue pigment, chromium oxide, chromium hydroxide, calamine, and carbon black.

5. The pressed powder cosmetic composition according to claim 1, wherein component (A) is at least one organic powder selected from the group consisting of polyamide, polyester, polypropylene, polystyrene, polyurethane, vinyl resin, urea resin, phenol resin, silicon resin, acrylic resin, melamine resin, epoxy resin, polycarbonate resin, divinylbenzine styrene copolymer, silk powder, cellulose powder, metal salts of along-chain alkyl phosphoric acid, and N-mono(long chain)alkylacyl basic amino acid.

6. The pressed powder cosmetic composition according to claim 1, wherein the fluorine compound of component (A) is a polyfluoroalkylphosphoric acid represented by the following formula (A):

$$[C_xF_{2x+1} C_y H_{2y} O]_z PO(OH)_{3-z} \quad (a).$$

wherein, x stands for 1 to 20, y stands for 1 to 5, and z stands for 1 or 2.

7. The pressed powder cosmetic composition according to claim 1, wherein the fluorine compound of component (A) is at least one member selected from the group consisting of fluoroalkyldi(oxyethyl)amine phosphate ester, fluoroalkyl-containing polymer, fluorine resin, fluoroalcohol, perfluoroepoxy compound, ethylene tetrafluoride, sulfoamide-type fluorophosphoric acid, perfluorosulfate salt, perfluorocarboxylate salt, perfluoroalkylsilane, silane coupling agent, LP- 1T, LP-4T, LP-8T, fluorine-containing halogenated hydrocarbon, trichlorotrifluoroethane, fluoroalkyl-containing polyhydric alcohol, fluoroalkyl-containing polyoxyethylene compound, fluoroalkyl-containing sulfoamide carboxylic acid, and fluoroalkyl-containing acrylate ester copolymer.

8. The pressed powder cosmetic composition according to claim 1, wherein the fluorine compound of component (A) is present in an amount of from 0.05 to 20 parts by weight.

9. The pressed powder cosmetic composition according to claim 1, wherein the fluorine compound of component (A) is present in an amount of from 2 to 10 parts by weight.

10. The pressed powder cosmetic composition according to claim 1, wherein component (A) is present in an amount of at least 50% by weight of the total powder.

11. The pressed powder cosmetic composition according to claim 1, wherein component (A) is present in an amount of from 55 to 99.9% by weight of the whole composition.

12. The pressed powder cosmetic composition according to claim 1, wherein component (A) is present in an amount of from 65 to 99.9% by weight of the total composition.

13. The pressed powder cosmetic composition according to claim 1, wherein component (A) is present in an amount of from 75 to 99.9% by weight of the total composition.

14. The pressed powder cosmetic composition according to claim 1, wherein component (B) has a modulus of elasticity of from 1 to 200 kg/cm².

15. The pressed powder cosmetic composition according to claim 1, wherein component (B) has a modulus of elasticity of from 1 to 100 kg/cm².

16. The pressed powder cosmetic composition according to claim 1, wherein component (B) has a molecular weight ranging from 10,000 to 1,000,000.

17. The pressed powder cosmetic composition according to claim 1, wherein component (B) has at least one monomer selected from the group consisting of a polymerizable double bond, poly(N-acylalkyleneimine)-modified silicone, and vinyl-silicone block polymer.

18. The pressed powder cosmetic composition according to claim 1, wherein component (B) has at least one monomer selected from the group consisting of ethylenically- unsaturated carboxylic acid, acrylic acid, methacrylic acid, maleic acid, fumaric acid, unsaturated carboxylate ester, hydroxyethyl(meth)acrylate, polyethylene glycol mono (meth)acrylate, unsaturated carboxylic amide, (meth) acrylamides, N-diacetone acrylamide, amino-containing unsaturated carboxylate ester, aminoethyl(meth)acrylate, N,N-diethylaminoethyl (meth)acrylate, N,N-diethylaminoethyl (meth)acrylate, N,N,N-trimethylaminoethyl (meth)acrylate, aromatic vinyl compound, styrene, α-methylstyrene, chlorostyrene, alkylstyrene, acrylate ester, methacrylate ester, methyl (meth)acrylate, ethyl (meth)acrylate, propyl (meth)acrylate, butyl (meth)acrylate, 2-ethylhexyl (meth)acrylate, t-butyl (meth)acrylate, 2-ethylhexyl (meth)acrylate, t-butyl (meth) acrylate, cyclohexyl (meth)acrylate, vinyl cyanide, acrylonitrile, methacrylonitrile, vinyl ester, vinyl acetate, vinyl halide, vinyl chloride, vinylidene chloride, fluorine monomer, trifluoroethyl methacrylate, 2,2,3,3-tetrafluoropropyl methacrylate, 2,2,3,3,4,4-hexafluorobutyl methacrylate, perfluorooctyl methacrylate, perfluorooctyl acrylate, and salts thereof.

19. The pressed powder cosmetic composition according to claim 1, wherein (B) comprises at least one poly(N-acylalkyleneimine) segment having the following formula:

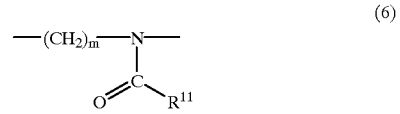

(6)

wherein, $R^{11}$ represents a hydrogen atom or a $C_{1-22}$ alkyl, cycloalkyl, aralkyl or aryl group and m stands for 2 or 3, and an organopolysilioxane segment.

20. The pressed powder cosmetic composition according to claim 19, wherein the poly(N-acylalkyleneimine) segment is bonded to the organopolysiloxine segment at the end thereof or as the side chain thereof through a hetero-atom-containing alkylene group.

21. The pressed powder cosmetic composition according to claim 1, wherein (B) is at least one vinyl-silicone block polymer having the following formula:

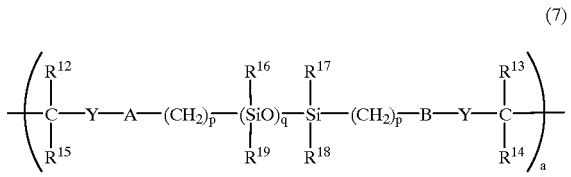

(7)

wherein, $R^{12,}$ $R^{13,}$ $R^{14,}$ and $R^{15}$ are the same or different and each independently represents a hydrogen atom, a $C_{1-6}$ alkyl group or a nitrile group, $R^{16,}$ $R^{17,}$ $R^{18,}$ and $R^{19}$ are the same or different and each independently represents a hydrogen atom, an alkyl, an aryl group, an aryl group substituted with a halogen, Y represents a linear or branched saturated or unsaturated $C_{1-10}$ hydrocarbon group which may be substituted by a halogen atom, A represents a —CONH—or —COO—group, B represents an —NHCO—or —OCO—group with the proviso that when A represents a —CONH— group then B represents a —NHCO— group and when A represents a —COO— group then B represents an —OCO— group, q ranges from 0 to 200, p ranges from 0 to 6, a ranges from 2 to 300; and a vinyl monomer unit free of a fluorine atom.

22. The pressed powder cosmetic composition according to claim 1, wherein component (B) is present in an amount of from 0.1 to 15% by weight of the total composition.

23. The pressed powder cosmetic composition according to claim 1, wherein component (B) is present in an amount of from 0.5 to 10% by weight of the total composition.

24. The pressed powder cosmetic composition according to claim 1, wherein component (B) is present in an amount of from 1 to 8% by weight of the total composition.

25. The pressed powder cosmetic composition according to claim 1, wherein component (C) is at least one fluorine oil selected from the group consisting of perfluoropolyether, perfluorodecalin, perfluorooctane, fluorine-modified silicone oil, FOMBLIN, and DEMNUM.

26. The pressed powder cosmetic composition according to claim 1, wherein component (C) is present in an amount of at least 50% by weight of a total oil concentration.

27. The pressed powder cosmetic composition according to claim 1, wherein component (C) is present in an amount of from 0.1 to 30% by weight of the total composition.

28. The pressed powder cosmetic composition according to claim 1, wherein component (C) is present in an amount of from 0.5 to 25% by weight of the total composition.

29. The pressed powder cosmetic composition according to claim 1, wherein component (C) is present in an amount of from 0.5 to 20% by weight of the total composition.

30. The pressed powder cosmetic composition according to claim 1, further comprising at least one solid or semi-solid selected from the group consisting of vaseline, lanolin, ceresin, microcrystalline wax, carnuba wax, candelilla wax, higher fatty acids, higher alcohols, liquid oil, squalane, liquid paraffin, ester oil, diglyceride, triglyceride, and silicon oil.

31. The pressed powder cosmetic composition according to claim 2, wherein the hardness is from 10 to 75.

32. The pressed powder cosmetic composition according to claim 2, wherein the hardness is from 10 to 70.

33. The pressed powder cosmetic composition according to claim 2, wherein the hardness is from 10 to 67.

34. The pressed powder cosmetic composition according to claim 2, wherein the hardness is from 30 to 75.

35. The pressed powder cosmetic composition according to claim 2, wherein the hardness is from 50 to 75.

36. The pressed powder cosmetic composition according to claim 2, wherein the porosity is from 0.37 to 0.5.

37. The pressed powder cosmetic composition according to claim 2, wherein the impact resistance is at least 7.

38. The pressed powder cosmetic composition according to claim 1, further comprising at least one member selected from the group consisting of a surfactant, antiseptic, antioxidant, colorant, thickener, pH regulator, perfume, ultraviolet absorber, humectant, blood flow promoter, coolant, antiperspirant, bactericide, and skin activator.

39. The pressed powder cosmetic composition according to claim 1, made by a process comprising:
mixing (A), (B), (C) with a volatile solvent.

40. The pressed powder cosmetic composition according to claim 39, wherein the volatile solvent is at least one member selected from the group consisting of water, low-boiling point alcohol, ethanol, isopropyl alcohol, hexane, isoparaffin, acetone, ethyl acetate, and volatile silicone oil.

41. The pressed powder cosmetic composition according to claim 39, wherein component (A) is mixed in an amount of from 40 to 94.9% by weight.

42. The pressed powder cosmetic composition according to claim 39, wherein component (A) is mixed in an amount of from 50 to 94.9% by weight.

43. The pressed powder cosmetic composition according to claim 39, wherein component (B) is mixed in an amount of from 0.1 to 14% by weight.

44. The pressed powder cosmetic composition according to claim 39, wherein component (B) is mixed in an amount of from 0.5 to 10% by weight.

45. The pressed powder cosmetic composition according to claim 39, wherein the volatile solution is mixed in an amount of from 5 to 40% by weight.

46. The pressed powder cosmetic composition according to claim 39, further comprising evaporating the volatile solvent.

47. The pressed powder cosmetic composition according to claim 39, further comprising molding the mixture under pressure and then evaporating the volatile solvent.

* * * * *